United States Patent
Schulz

Patent Number: 5,806,822
Date of Patent: Sep. 15, 1998

[54] HOLDER FOR MEDICAL SUCTION INSTRUMENT

[76] Inventor: Robert R. Schulz, 2907 N. Portage Ave., Grayling, Mich. 49738

[21] Appl. No.: 630,218

[22] Filed: Apr. 10, 1996

[51] Int. Cl.$^6$ ........................................ A47F 5/00
[52] U.S. Cl. ........................ 248/309.1; 248/223.41; 248/315; 211/70.6
[58] Field of Search ............... 248/176.1, 223.41, 248/309.1, 315; 211/62, 67, 68, 70.6

[56] References Cited

U.S. PATENT DOCUMENTS

| | | | |
|---|---|---|---|
| D. 235,486 | 6/1975 | Van den Bergh | D83/1 B |
| D. 265,508 | 7/1982 | Rusteberg | D24/52 |
| D. 300,406 | 3/1989 | Bordian | D8/367 |
| D. 301,976 | 7/1989 | Greenhut et al. | D8/373 |
| D. 313,341 | 1/1991 | Gaboriault et al. | D8/366 |
| D. 314,325 | 2/1991 | Ziaylek, Jr. et al. | D8/373 |
| D. 335,925 | 5/1993 | Newman | D24/128 |
| D. 354,350 | 1/1995 | Pryor et al. | D24/128 |
| 424,041 | 3/1890 | Ward . | |
| 444,769 | 1/1891 | Sherman . | |
| 800,033 | 9/1905 | Ullrich . | |
| 1,206,655 | 11/1916 | Belcher . | |
| 4,219,178 | 8/1980 | Assion | 248/314 |
| 4,278,225 | 7/1981 | Phelps | 248/311.3 |
| 4,304,382 | 12/1981 | Jelen | 248/221.1 |
| 4,586,615 | 5/1986 | Quitmann | 211/70.6 |
| 4,606,735 | 8/1986 | Wilder et al. | 604/180 |
| 4,732,147 | 3/1988 | Fuller | 128/207.18 |
| 4,997,421 | 3/1991 | Palsrok et al. | 604/174 |
| 5,046,622 | 9/1991 | Wood | 211/63 |

Primary Examiner—Daniel P. Stodola
Assistant Examiner—Richard M. Smith
Attorney, Agent, or Firm—Van Dyke, Gardner, Linn & Burkhart, LLP

[57] ABSTRACT

A holder for supporting a medical suction instrument generally upright on a wall or other support surface for storage and reuse, generally near a patient's location. The holder has a base and spaced supports extending outwardly preferably from upper and lower ends of the base. The upper support preferably includes a continuous rim such as an annular ring defining a first opening for receiving a first portion of the instrument. The lower support preferably has spaced support arms defining a second opening with an access to that second opening at the outer ends of the support arms. A second portion of the instrument is engaged by the upper support surfaces of the support arms while other portions of the instrument are inserted through the access and extend out of the second opening below the holder.

24 Claims, 3 Drawing Sheets

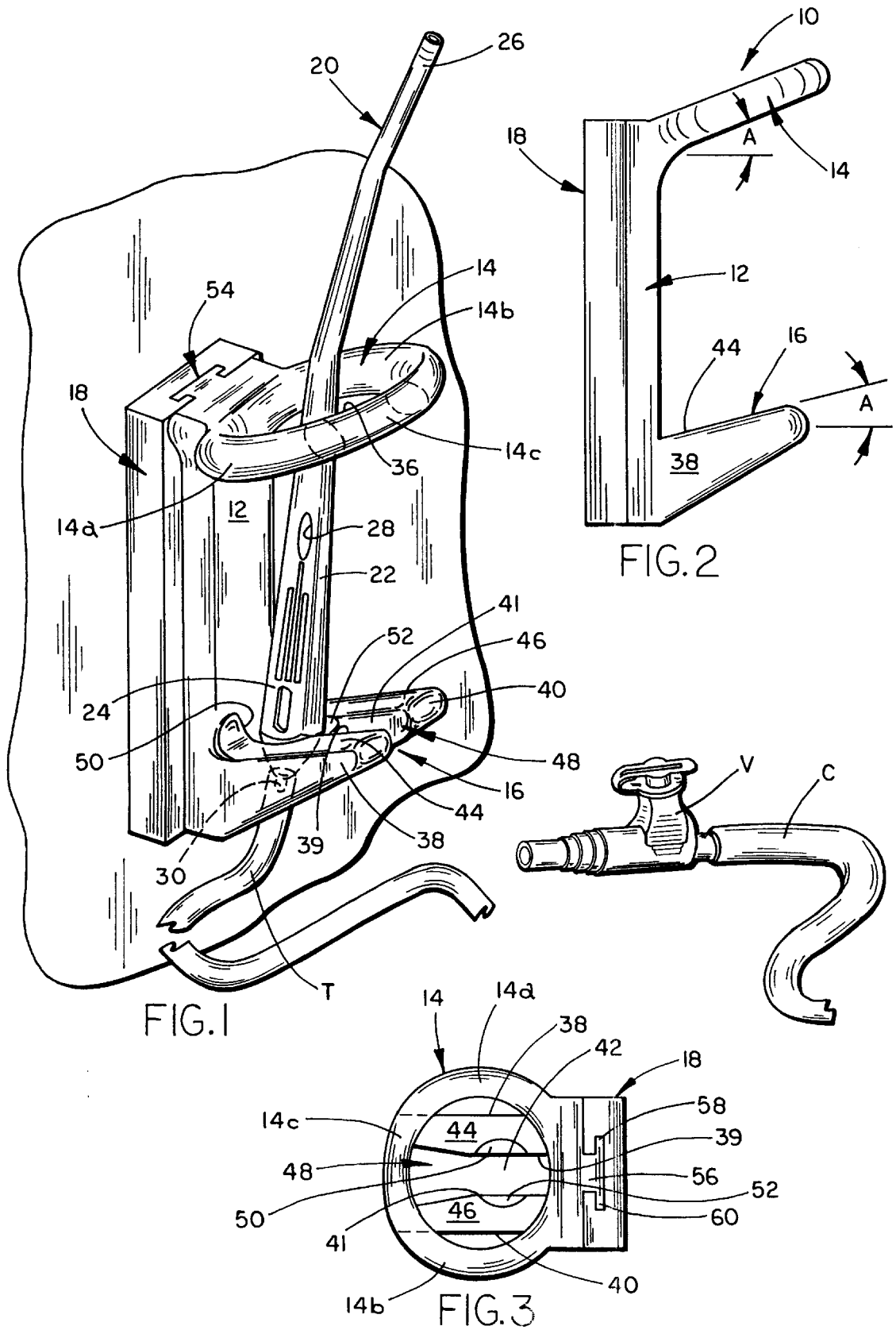

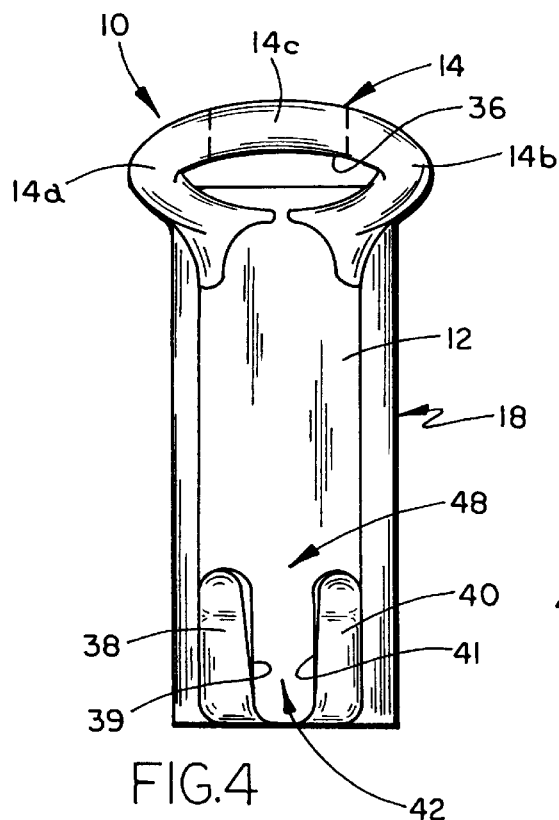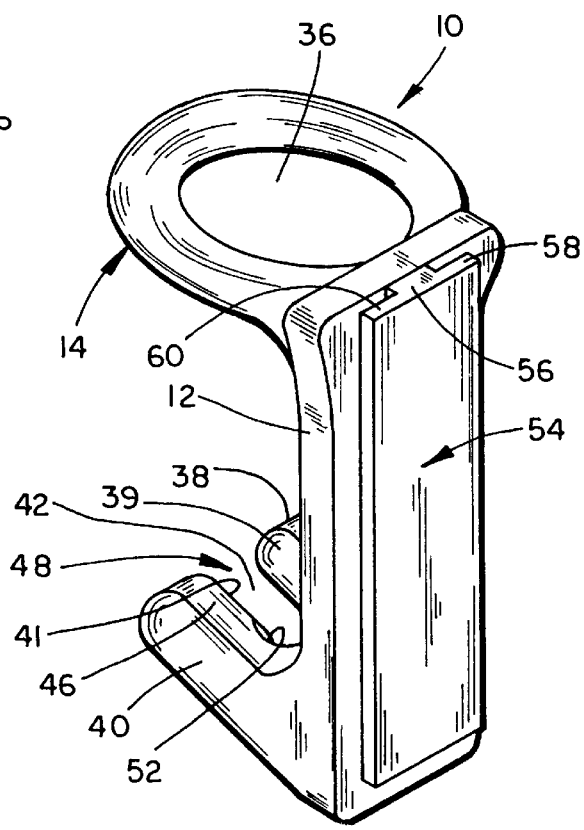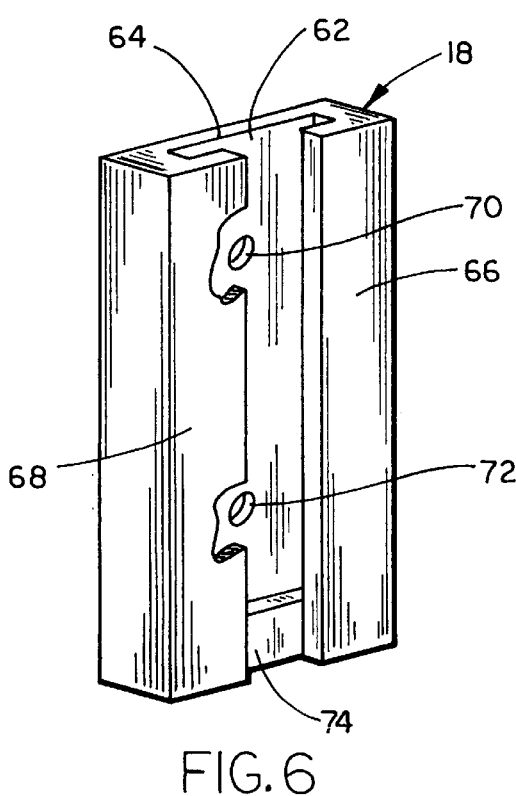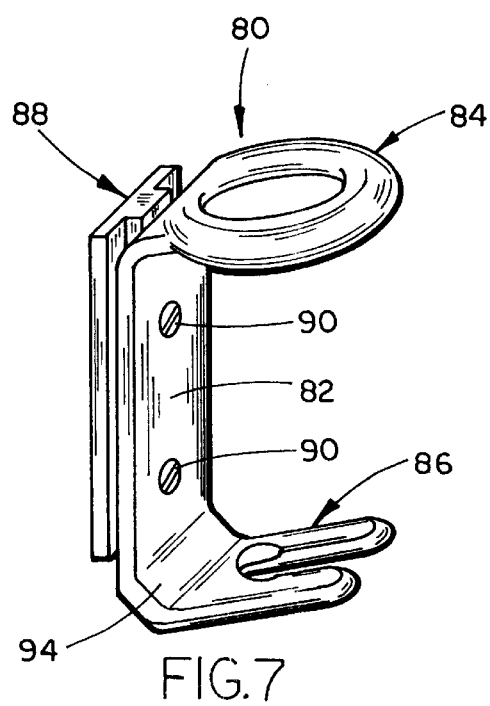

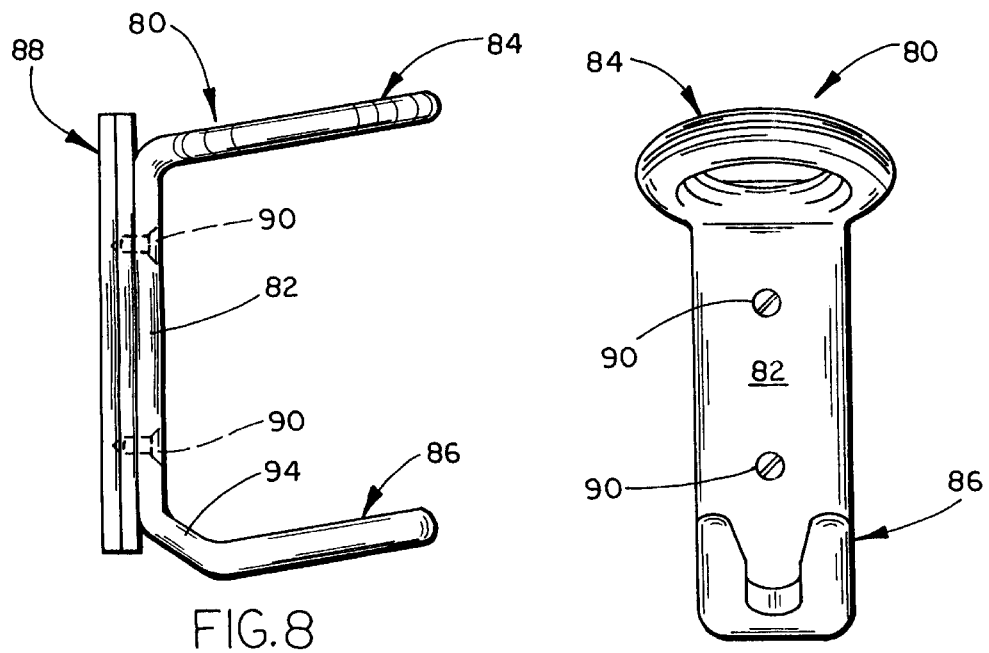
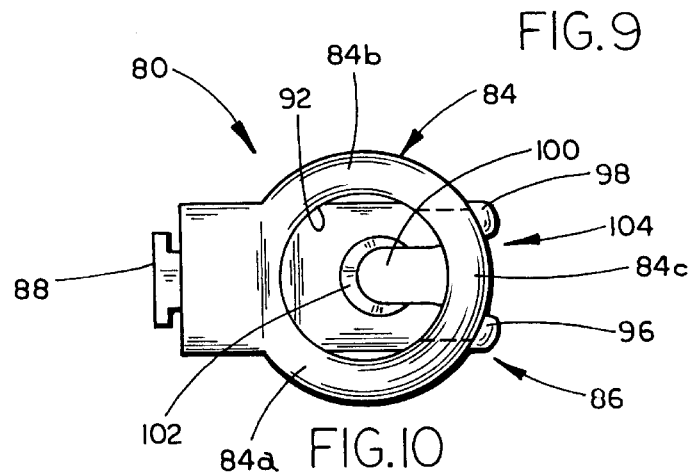
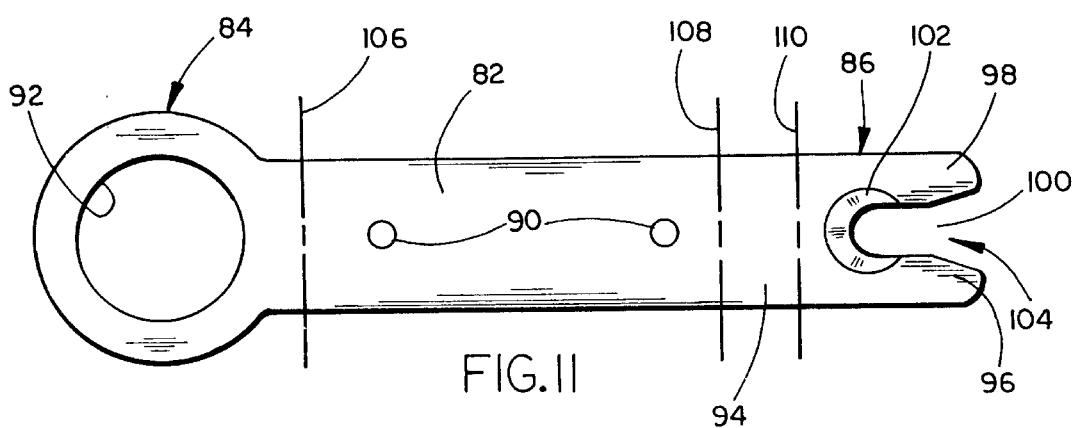

HOLDER FOR MEDICAL SUCTION INSTRUMENT

FIELD OF THE INVENTION

This invention relates to supports for holding medical instruments when not in use and, more particularly, to a holder adapted for mounting in an upright position to support a medical suction instrument for storage and reuse proximate a patient's position while allowing easy insertion and removal.

BACKGROUND OF THE INVENTION

Medical suction instruments are commonly used in hospitals, clinics, long-term care centers and other medical facilities for removing excess fluids from patients such as those suffering from paralysis and the like. A commonly known and widely used instrument of this type is the Yankauer suction instrument which has an elongated, hollow body terminating in an angled hollow tip. An opening through a side wall of the hollow body may be closed by the thumb or forefinger of the user to create suction through the tip. When in use, fluids are drawn through the tip and hollow body when the opening is closed and pass through a reduced diameter neck at the lower end of the instrument to which is attached a suction hose leading to a vacuum or suction source and a receptacle for the fluids.

After use, the Yankauer suction instrument, is usually placed in a portion of the envelope in which the instrument is purchased. The envelope is pulled over the hollow tip and the instrument is placed on the patient's bed while the patient is helped to perform other functions. If the instrument is not held tightly under a pillow or in some other position, it can easily fall to the floor or become soiled. This requires replacement of the instrument thereby adding cost to the care of the patient or for the hospital. Therefore, a need was apparent for a convenient method for storing and maintaining a medical instrument such as a Yankauer suction instrument in a clean and ready position for reuse.

In addition, a nurse or medical aid often fails to disconnect the suction tubing from the suction instrument prior to putting on sterile gloves. The removal of the suction tubing from the instrument is often necessary to allow attachment of a sterile suction catheter, bronchial suction tube or other device used on internal portions of the body. In order to detach the tubing after sterile gloves have been put on, it was previously necessary to grasp both the instrument and the tube using both hands thereby breaking the sterile condition and requiring new sterile gloves. Accordingly, a need was also apparent for holding medical suction instruments in such a manner that removal of suction tubing from the instrument could be accomplished without requiring two hands or breaking the sterile technique, while allowing one hand to remain sterile to attach a sterile suction catheter, bronchial suction tube, or the like.

In addition, prior known methods of supporting medical suction instruments on flat or substantially flat surfaces such as the patient's bed while performing other tasks often allowed the fluid remaining in the suction instrument to drain out of the instrument thereby soiling undesired areas around the patient.

The present invention was conceived in recognition of, and as a solution for, the above and related problems encountered during the use of these medical suction instruments.

SUMMARY OF THE INVENTION

Accordingly, the present invention provides a holder for supporting a medical suction instrument generally upright on a wall or other support surface for storage and/or reuse generally proximate a patient location. The holder allows the medical suction instrument to be supported in an upright position to avoid undesired drainage or leakage therefrom when the instrument is not in use and yet maintains the instrument in an easily accessible, clean position which does not interfere with other tasks which must be performed for the patient. In addition, the holder provides a device for securely retaining the instrument without requiring the instrument to be physically grasped by the user so that the suction tubing used with such instrument can be removed from the instrument while maintaining at least one hand of the user in a sterile condition so that a sterile catheter, bronchial suction tube, or the like can be attached without totally breaking sterile technique.

In one form, the invention is a holder for supporting a medical instrument in a generally upright position including a base adapted to be supported in an upright, generally vertical position on a mounting surface, a first support at a first location on the base, and a second support at a second location on the base. The first support extends outwardly from the base in a predetermined direction and includes a first opening for receiving a first portion of the medical instrument. The second support extends outwardly from the base generally in the same predetermined direction and includes a second opening having an access opening outwardly away from the base such that a portion of the medical instrument can be inserted into the second opening through the access. The second support has a support surface adjacent the second opening for supporting a second portion of the medical instrument. The second support is spaced from the first support. Thus, the first and second supports maintain the medical instrument in a generally upright position when inserted in the first and second openings.

In preferred aspects of the invention, the first support may include a continuous rim defining the first opening, such as an annular ring. The second support preferably includes a pair of spaced arms, the support arms each having an upper surface facing the first support member for engaging and supporting the medical instrument. The support arms are spaced from one another to define a second opening for receiving a second portion of the medical suction instrument. The second opening opens upwardly toward the first support member, downwardly away from the first support member and outwardly away from the base. Further, both the annular ring and spaced support arms are preferably inclined upwardly in a direction extending away from the base to further insure retention of the medical instrument. In addition, a recess in the support surfaces of the spaced support arms engages and resists withdrawal of that portion of the medical suction instrument.

The holder of the present invention may be injection molded in one piece from resinous plastic or may be bent from a formed pattern in a sheet of plastic. In either case, the support may be fastened directly to a support surface such as a wall or be joined to a slide mount adapted for slidable reception in a wall bracket. In the latter form, the bracket is secured to the wall or support surface and the holder of the present invention may be easily inserted therein or removed for cleaning, sterilization or repair as required without the need for removal of any fasteners.

Accordingly, the present invention overcomes numerous problems encountered previously with the use of medical suction instruments and provides a holder allowing easy insertion and removal of the suction instrument for use when desired, the holder being easily mounted proximate a patient location in a hospital, clinic, long-term care facility, or even in a mobile treatment vehicle such as an ambulance. The instrument is easily inserted through the opening in the upper support member while the lower end of the instrument is moved into support position on the lower support member or support arms through the access opening such that any tubing connected to the instrument projects below the holder. The holder, therefore, supports the instrument with its suction tip extending upwardly to prevent undesired drainage or leakage of fluids therefrom, while positioning the instrument for removal of the suction tubing without requiring the use of both hands thereby preventing the need to break sterile technique. The holder also allows better sanitation in the use of medical suction instruments and reduces the need for repair or replacement due to breakage if dropped or left in insecure positions on conventional supports.

These and other objects, advantages, purposes and features of the invention will become more apparent from a study of the following description taken in conjunction with the drawings.

BRIEF DESCRIPTION OF THE DRAWINGS

FIG. 1 is a perspective view of a first embodiment of the holder for medical suction instruments of the present invention slidably mounted in a wall mounting bracket and illustrating support of a Yankauer suction instrument thereon with the suction tubing projecting below the holder;

FIG. 2 is a side elevation of the holder and wall mounting bracket of FIG. 1;

FIG. 3 is a top plan view of the holder and wall mounting bracket of FIGS. 1 and 2;

FIG. 4 is a front elevation of the holder and wall mounting bracket of FIGS. 1–3;

FIG. 5 is a rear perspective view of the holder of FIG. 1 when removed from the wall mounting bracket;

FIG. 6 is a front perspective view of a wall bracket for slidably mounting the holder of FIGS. 1–5;

FIG. 7 is a perspective view of a second embodiment of the holder for medical suction instruments, shown without the wall mounting bracket;

FIG. 8 is a side elevation of the holder of FIG. 7;

FIG. 9 is a front elevation of the holder of FIGS. 7 and 8;

FIG. 10 is a top plan view of the holder of FIGS. 7–9; and

FIG. 11 is a plan view of a blank formed from sheet plastic prior to bending into the holder of FIGS. 7–10.

DESCRIPTION OF THE PREFERRED EMBODIMENTS

Referring now to the drawings in greater detail, FIGS. 1–6 illustrate a first embodiment 10 of the holder for medical suction instruments of the present invention. Holder 10 includes a base 12, a first support 14 at the upper end of base 12, and a second support 16 at the lower end of the base. An elongated mounting bracket 18 is adapted to slidingly receive the holder 10 on a wall or other support surface which, preferably, is generally vertically oriented. As explained below, holder 10 is adapted to support and retain an elongated medical instrument such as a Yankauer suction instrument 20 of the type shown in FIG. 1, which instrument forms no part of the present invention.

The typical medical suction instrument 20 used with the present holder includes an elongated hollow body 22 which generally tapers in conical fashion from a wider lower end 24 to an angled, hollow tip 26. An opening 28 extending through the side wall of body 22 into the hollow interior is provided along the length of the body and is adapted to be covered with the user's thumb or forefinger. At the lower end of body 22 is a reduced diameter neck 30 adapted to telescopingly receive a suction tube T to apply a vacuum or suction from a vacuum source (not shown). With suction tube T connected to neck 30, air will be drawn through larger opening 28 instead of smaller tip 26. However, when the user closes opening 28 with his/her thumb or forefinger, suction is applied through tip 26 to allow removal of fluids from a patient through tube T. During the course of treatment of a patient, it is some times necessary to remove tube T from suction instrument 20 and apply the suction end of the tube to a suction catheter C including a valve V for use with a patient. Holder 10, as shown in FIG. 1, is adapted to support the suction instrument 20 in a generally upright, vertical position such that fluids withdrawn using the instrument do not leak or drain from tip 26 or opening 28 in an undesired manner when the instrument is not in use. Likewise, holder 10 allows the instrument to be retained while the user withdraws tube T from neck 30 using only one hand such that the other hand which may already be in a sterile glove can be used to hold the sterile suction catheter C while the tube T is applied to valve V. Thus, holder 10 eliminates the need for breaking the sterile condition of both hands after sterile gloves have been put on by the user.

As is best seen in FIGS. 2–5, holder 10 is preferably injection molded from a suitable resinous plastic material and includes rounded or beveled edges for ease in cleaning. Base 12 is generally rectangular and elongated in a vertical direction. Support 14 extends outwardly at an upwardly inclined angle A and includes a continuous rim which, as shown in FIGS. 1–5, is preferably an annular ring having a circular cross section in the shape of a donut. Rim or ring 14 includes curved side members 14A, 14B which extend outwardly from the base, which side members are preferably connected by a front curved rim portion 14C (which extends between the dotted lines in FIGS. 1, 3 and 4). As will be understood, however, it is within the scope of the present invention to provide the upper support 14 including only side members 14A, 14B without the continuous front rim portion 14C. In such case, an access to the opening between side members 14A, 14B would be at the position of front rim portion 14C. In addition, upper member 14 could have a shape other than circular or annular, such as V-shaped, square, rectangular or the like. In any case, the support, rim or ring defines a space or opening 36 adapted to receive and support the upper end of instrument 20 and prevent it from tipping over laterally in a plane generally parallel to the front surface of base 12. When front rim portion 14C is included as in the preferred embodiment, ring 14 totally confines the upper end of instrument 20 to prevent the instrument from tipping laterally or falling forwardly out of the holder in a direction away from base 12. Of course, the support, rim or ring itself can have cross sectional shapes other than circular such as triangular, rectangular, square, pentaganal or the like.

Spaced below and in alignment with upper support 14 at the lower end of base 12 is lower support 16. Preferably, support 16 includes a pair of parallel, spaced support arms 38, 40 which define an instrument receiving space or opening 42 therebetween. Support arms 38, 40 are each generally triangular in shape when viewed from the side (FIG. 2) and include generally rectilinear top support surface 44, 46. In the preferred embodiment, the outer ends of arms 38, 40 are rounded and taper to a thinner section at the outer ends as compared to the thickness of the inner ends which are joined to base 12 (FIG. 3). Such tapering provides a wider access 48 to space or opening 42 facilitating the insertion of the lower end 24, 30 of suction instrument 20 when the instrument is placed on holder 10. Preferably, the upper support surfaces of support arm 38, 40 are inclined upwardly as they progress away from base 12 at the same angle A as is support member 14 such that the planes of support member 14 and upper surfaces 44, 46 of support arms 38, 40 are generally parallel.

As is best seen in FIGS. 1, 3 and 5, upper support surfaces 44, 46 of support arms 38, 40 each include a curved indentation 50, 52, which indentations are aligned with one another across space 42 to define a recess or pocket which receives the lower end of instrument 20 as shown in FIG. 1. Each support arm 38, 40 includes an inner surface 39, 41. Indentations 50, 52 are preferably formed at the corner of inner surfaces 39, 41 and upper support surfaces 44, 46 by beveling or chamfering a section of the corner between such surfaces. The pocket or recess defined by aligned indentations 50, 52 receives the rounded lower end of body 24 of medical instrument 20 and confines that lower end in its desired support position as shown in FIG. 1. The weight of suction tubing T connected to the lower end 30 of instrument 20 exerts a downward force on the instrument to help hold the instrument in place in the recess while the recess, combined with the upwardly inclined angle A of support surfaces 44, 46 of arms 38,40, resists movement of the instrument away from base 12 to further prevent undesired tipping or release of the instrument 20. As will be seen best in FIGS. 2 and 3, the outer diameter of upper support ring 14 is substantially the same or slightly greater than the length of support arms 38 from base 12 to their outer ends. In addition, as is best seen in FIG. 3, the recess defined by indentations 50, 52 is preferably formed in support surfaces 44, 46 of arms 38, 40 in vertical alignment with opening 36 of ring 14 such that instrument 20 will be supported in a generally upright position as shown.

As shown in FIGS. 1, 3 and 5, a mounting member 54 is molded integrally on the rear surface of body 12 opposite the front surface from which supports 14, 16 extend outwardly. Mounting member 54 is an elongated slide mount having a T-shaped cross section including a center 56 and outwardly extending flanges 58, 60 which are spaced away from the rear surface of base 12. The length of mounting member 54 is slightly less than the overall length of the rear surface of body 12 as shown in FIG. 5.

Mounting member 54 on holder 10 is adapted to slidingly mate with a T-shaped receptacle 62 in wall bracket 18 as shown in FIGS. 1, 3 and 6. Bracket 18 includes a generally rectangular rear wall 64 and a pair of spaced inwardly extending L-shaped flanges 66, 68 which define an elongated, outwardly opening, T-shaped receptacle 62. A pair of screw receiving mounting apertures 70, 72 extend through rear wall 64 to receive screws for mounting bracket 18 on a wall or other vertically oriented support surface such as in a hospital, clinic, ambulance or the like. At the lower end of receptacle 62 is a stop wall or shoulder 74 having a thickness equivalent to receptacle 62. When mounting member 54 is slidably inserted in the open top of receptacle 62, flanges 58, 60 are received in the receptacle and allow the mounting member, and the holder 10 to which it is attached, to slide downwardly until the lower end of mounting member 54 contacts shoulder 74 to prevent further downward movement. At such position, the top surface of mounting member 54 is flush with the upper surface of bracket 18 as shown in FIGS. 1–4. Thus, once bracket 18 is mounted on a support surface with appropriate fasteners using apertures 70, 72, holder 10 may be repeatedly slidably inserted or removed from receptacle 62 of the bracket via mounting member 54 to allow cleaning, sterilization or replacement.

With reference to FIGS. 7–11, an alternate embodiment 80 of the holder for medical suction instruments is illustrated. Holder 80 includes similar elements to those included in holder 10 but is adapted to be formed by bending of a configured blank of sheet plastic or acrylic material as shown in FIG. 11. Holder 80 includes a base 82, upper support member 84, and lower support member 86. An elongated, T-shaped mounting member 88, preferably formed from wood or molded plastic, is preferably secured to the rear surface of base 82 by a pair of spaced threaded fasteners or screws 90. Alternately, mounting member 88 can be secured with suitable adhesive or with other attachment methods.

Upper support member 84 extends outwardly from the upper end of base 82 at an upwardly inclined angle (FIGS. 7–9) and includes a continuous annular ring defining a circular opening 92. Side members 84A, 84B are joined by end section 84C to define the continuous ring.

Spaced below upper support member 84 is lower support member 86 at the lower end of base 82. Lower support member 86 includes a downwardly angled support flange 94 from which extend a pair of parallel support arms 96, 98 defining space 100 therebetween. The closed end of the space 100 includes a chamfer or countersunk circular area or indentation 102 defining a recess or pocket providing a support area for the lower end of medical instrument 20 when received therein. The rounded outer tips and taper of arms 96, 98 define access 104 to space 100 therebetween allowing insertion of the lower end of the medical instrument and any attached tube T as noted above. Support arms 96, 98 are also angled upwardly generally at the same angle as upper support member 84 such that the upper support surfaces of the support arms are generally parallel to the upper member. As is best seen in FIG. 10, recess 102 is generally centrally aligned with the opening 92 in upper member 84 such that when the elongated medical instrument 20 is received in the upper and lower support members, it will be supported in a generally upright position in a manner similar to that shown in FIG. 1.

As is best seen in FIG. 11, the plastic sheet material from which holder 80 is formed is preferably cut from a larger sheet to have a generally key hole shaped configuration. Annular 84 ring is formed at one end and includes circular opening 92 cut or formed therein. A slightly tapered slot is formed in the opposite end to provide space 100 and indentation 102 is countersunk at the closed end of space 100. Thereafter, the plastic sheet can be heated and formed or bent along spaced lines 106, 108, 110 to form the upper support member 84, lower support member 86 and support arms 96, 98. Thereafter, the preformed T-shaped slide mount 88 can be secured by screws received through apertures 90 or with other attachment methods and the holder 80 is then complete.

As will be appreciated, holder 80, when formed from the sheet material as described above, is less expensive than molded holder 10 and can be easily inserted in a wall bracket such as that shown at 18 in FIG. 6 adapted for mounting on a vertical support surface such as a wall. Holder 80 can then be slidably inserted and removed from the wall bracket for cleaning, sterilization or replacement. However, in view of its lesser expense, it may be more readily replaced if damaged or broken. As with holder 10, the edges of holder 80 are preferably rounded or chamfered to facilitate cleaning and sanitation.

Use of holders 10, 80 is made in the same manner. As will be understood from FIG. 1, once holder 10 or 80 is slidably mounted on bracket 18 on a wall or other vertically oriented support surface, medical suction instrument 20 may be grasped with one hand in the area of hollow body 22. The instrument is tipped to insert the upper end or tip 26 under support ring 14 or 84 through opening 36 or 92. The upwardly inclined angle of support member 14 or 84 facilitates insertion of the instrument into opening 36 or 92. It will be apparent that opening 36 or 92 can be made smaller if the angle of the upper support member is increased thereby allowing easier insertion of the tip. After the upper end of the instrument is inserted in the upper opening, the lower end of the instrument including tube T is rotated through access 48 or 104 into space 42, 100 until the area of indentations 50, 52 or 102 is reached. The instrument is then lowered until the rounded lower end of body portion 24 is received in the indentations with tube T extending downwardly from opening 42, 100 to a position below the holder 10, 80. The weight of tube T attached to the instrument 20 helps retain the lower end in indentations 50, 52 or 102 to resist movement and withdrawal from the lower support. The upper end of the instrument is confined within the opening 36, 92 and prevented from tipping laterally or forwardly out of the holder. Thus, instrument 20 will be held in a generally upright position generally parallel to the front surface of base 12 or 82 until reuse or removal from the holder is required. Bracket 18 may be positioned proximate to the location of a patient's bed or other support so that the suction instrument can be easily reached by a medical attendant or nurse and used with the patient followed by easy return and insertion into the holder 10, 80. When held upright after use, any remaining fluids in the instrument will not leak or drain from tip 26 or body 24 but will be disposed of through suction tube T. Even when tube T is not connected to the instrument it will rest in indentations 50, 52 or 102 and upper openings 36, 92 for proper support. The outwardly opening space 42, 100 provided by tapered access 48 or 104 allows for ease in insertion since tube T need not be disconnected from the instrument before insertion in the holder and, therefore, allows easy access for reuse while leaving tube T in its connected position.

While several forms of the invention have been shown and described, other forms will now be apparent to those skilled in the art. Therefore, it will understood that the embodiments shown in the drawings and described above are merely for illustrative purposes and are not intended to limit the scope of the invention which is defined by the claims which follow.

The embodiments of the invention in which an exclusive property or privilege is claimed are defined as follows:

1. A medical suction instrument holder which is adapted to hold a medical suction instrument in a generally vertical, upright position, the instrument having an elongated body having an upper end terminating in a tip, a lower end, and a neck at said lower end, said neck receiving a suction tube for connection to a vacuum source for removal of fluids from a patient, said holder comprising:

a base having a top end and a bottom end and adapted to be supported in an upright, generally vertical position on a mounting surface with said top end being uppermost;

a first support adjacent said top end on said base, said first support extending outwardly from said base in a predetermined direction, and including a continuous rim having an open top side and an open bottom side and defining a first opening extending through said rim for receiving and confining the upper end of the medical suction instrument, said first opening being significantly larger than said upper end and tip of the medical suction instrument such that the upper end and tip thereof are easily inserted in said first opening from said open bottom side of said continuous rim and will protrude outwardly from said open top side of said continuous rim;

a second support at a second location spaced below and toward said bottom end on said base, said second support extending outwardly from said base generally in said predetermined direction, having an outer end, and including a second opening having an access opening outwardly away from said base such that the neck of the medical suction instrument can be inserted into said second opening through said access, said second support also having a support surface adjacent said second opening for supporting the lower end of the medical suction instrument, said support surface being inclined upwardly in a direction progressing from said base toward said outer end to resist movement of the lower end of the medical suction instrument away from said base while the neck and any suction tube thereon extend downwardly from said second opening;

whereby said first and second supports maintain the medical suction instrument in a generally upright position when inserted in said first and second openings while the weight of the medical suction instrument and said upward incline of said support surface of said second support resist movement of said lower end of said instrument off said second support.

2. The holder of claim 1 wherein said first support is an annular ring, said first opening being a circular aperture extending through said ring; said circular aperture being generally aligned with said support surface on said second support.

3. The holder of claim 2 wherein said ring has a diameter at least as long as the length of said support arms.

4. The holder of claim 1 wherein said support surface on said second support includes a recess which receives and helps resist movement of the lower end of the medical suction instrument therefrom.

5. The holder of claim 4 wherein said second support includes a pair of spaced support arms extending outwardly from said base below the position of said first support, said support arms each having a terminal end spaced away from said base, said terminal ends being spaced from one another and having divergent inner surfaces such that said access is wider than said second opening therebetween.

6. The holder of claim 5 wherein said base, first support and support arms are formed in one piece from a single plastic sheet, said first support and support arms being bent outwardly from spaced locations on one side of said sheet to define said base which extends therebetween.

7. The holder of claim 5 wherein said spaced support arms are each inclined upwardly in a direction progressing outwardly from said base.

8. The holder of claim 1 including a mount adapted to secure said holder in an upright position, said mount located on a surface of said base opposite said rim and support arms.

9. A medical suction instrument holder which is adapted to hold a medical suction instrument in a generally vertical, upright position the instrument having an elongated body having an upper end terminating in a tip, a lower end, and a neck at said lower end, said neck receiving a suction tube for connection to a vacuum source for removal of fluids from a patient, said holder comprising:

a base having a top end and a bottom end and adapted to be supported in an upright, generally vertical position on a support surface with said top end being uppermost;

an upper support member extending outwardly from said base adjacent said top end, said support member including a continuous rim inclined upwardly in a direction progressing outwardly from said base and having an open top side and an open bottom side and defining a first space for receiving and confining the upper end of the medical suction instrument said first space extending through said rim and being significantly larger than said upper end and tip of the medical suction instrument such that the upper end and tip thereof are easily inserted in said first space from said open bottom side of said continuous rim and will protrude outwardly from said open top side of said continuous rim; and a pair of support arms extending outwardly away from said base generally in said predetermined direction at a position spaced from and below said support member, said support arms each having an outer end and an upper surface facing said support member for engaging and supporting the lower end of the medical suction instrument, and being spaced from one another to define a second space for receiving the neck of the medical suction instrument and any suction tube thereon, said second space opening upwardly toward said support member, downwardly away from said support member, and outwardly away from said base, said upper surface on each support arm being inclined upwardly in a direction progressing from said base toward said outer end to resist movement of the lower end of the suction instrument away from said base;

whereby the medical suction instrument is easily inserted in said first and second spaces for support in a generally upright position on said holder.

10. The holder of claim 9 wherein said support arms include a recess which helps resist withdrawal of a portion of the suction instrument from said second space.

11. The holder of claim 10 wherein said recess includes a pair of indentations, one indentation on each support arm, said indentations being aligned with one another across said second space.

12. The holder of claim 11 wherein each support arm includes an inner edge facing said second space; each indentation being a chamfer on one of said inner edges of said support arms.

13. The holder of claim 10 wherein said support arms extend outwardly from a flange which extends outwardly from said base, said second space having a closed end at said flange, said recess including a pocket at said closed end of said second space.

14. The holder of claim 13 wherein said pocket is a countersunk area at said closed end of said second space.

15. The holder of claim 9 wherein said rim is an annular ring; said support arms being separate from one another to provide access to said second space therebetween.

16. The holder of claim 15 wherein said annular ring and said upper surface of each of said support arms are inclined upwardly generally at the same angle and are generally parallel to one another.

17. The holder of claim 16 wherein said ring has a diameter at least as long as the length of said support arms.

18. The holder of claim 9 including a mount adapted to secure said holder in an upright position, said mount located on a surface of said base opposite said rim and support arms.

19. The holder of claim 18 wherein said mount includes an elongated slide for slidably mounting said holder on a mounting bracket whereby said holder is removable for cleaning and/or replacement.

20. The holder of claim 19 in combination with a mounting bracket adapted to support said holder upright on a generally vertically oriented surface; said mounting bracket including a receptacle for slidably receiving said mount to secure said holder on the vertically oriented surface.

21. The holder of claim 9 wherein said base, support member, and support arms are formed in one piece from a single plastic sheet, said support member and support arms being bent outwardly from spaced locations on one side of said sheet to define said base which extends therebetween.

22. A medical suction instrument holder which is adapted to hold a medical suction instrument in a generally vertical, upright position, the instrument having an elongated body having an upper end terminating in a tip, a lower end, and a neck at said lower end, said neck receiving a suction tube for connection to a vacuum source for removal of fluids from a patient, said holder comprising;

a base having upper and lower ends and adapted to be supported in an upright, generally vertical position on a mounting surface with said upper end being uppermost;

a first support adjacent said upper end of said base, said first support extending outwardly from said base in a predetermined direction and including a continuous rim having an open top side and an open bottom side and defining a first opening extending through said rim for receiving and confining the upper end of the medical suction instrument, said first support including said continuous rim being inclined upwardly in a direction progressing outwardly from said base, said first opening being significantly larger than said upper end and tip of the medical suction instrument such that the upper end and tip thereof are easily inserted in said first opening from said open bottom side of said continuous rim and will protrude outwardly from said open top side of said continuous rim;

a pair of support arms extending outwardly away from said base generally in said predetermined direction at a position spaced below said first support, said support arms each having an outer end and an upper surface facing said first support for engaging and supporting the lower end of the medical suction instrument and being spaced from one another to define a second opening for receiving the neck at the lower end of the medical suction instrument, said support arms also defining an access to said second opening between said outer ends and a recess in said upper surface of each of said support arms, said upper surface on each support arm being inclined upwardly in a direction progressing from said base toward said outer end and including said recess aligned with said recess on the other of said support arms to resist movement of the lower end of the medical suction instrument away from said base;

whereby the medical suction instrument is supported generally upright by said first support and pair of support arms.

23. The holder of claim 22 wherein each of said recesses is an indentation, said indentations being aligned with one another across said second opening.

24. The holder of claim 23 wherein said support arms each have an inner surface defining said second opening, said inner surfaces being divergent such that said access is widest between said outer ends.

* * * * *

UNITED STATES PATENT AND TRADEMARK OFFICE
CERTIFICATE OF CORRECTION

PATENT NO. : 5,806,822
DATED : September 15, 1998
INVENTOR(S) : Robert R. Schulz It is certified that error appears in the above-identified patent and that said Letters Patent is hereby corrected as shown below:

In the Abstract, line 1:
    After "holder" insert --is disclosed--.

Column 5, line 16:
    "comer" should be --corner--

Column 5, line 18:
    "comer" should be --corner--

Column 9, line 9:
    After "instrument" insert --,--

Signed and Sealed this

Thirty-first Day of August, 1999

Attest:

Q. TODD DICKINSON

*Attesting Officer*      *Acting Commissioner of Patents and Trademarks*